(12) United States Patent
Castelli et al.

(10) Patent No.: US 6,589,535 B2
(45) Date of Patent: Jul. 8, 2003

(54) NUTRITIONAL SUPPLEMENT BASED ON BLACKCURRENT SEED OIL

(75) Inventors: Dominique Castelli, Paris (FR); Nathalie Issachar, Paris (FR)

(73) Assignee: Johnson & Johnson SA (FR)

( * ) Notice: Subject to any disclaimer, the term of this patent is extended or adjusted under 35 U.S.C. 154(b) by 0 days.

(21) Appl. No.: 09/764,737

(22) Filed: Jan. 17, 2001

(65) Prior Publication Data

US 2002/0044980 A1 Apr. 18, 2002

(30) Foreign Application Priority Data

Jan. 26, 2000 (FR) .............................. 0000975

(51) Int. Cl.⁷ ...................... A61K 47/44; A61K 31/355; A61K 31/34; A61K 31/015
(52) U.S. Cl. ................... 424/283.1; 514/474; 514/763; 514/458; 424/776
(58) Field of Search ................................ 424/450, 776, 424/283.1; 514/763, 885, 474, 458

(56) References Cited

U.S. PATENT DOCUMENTS

| | | | | |
|---|---|---|---|---|
| 4,970,235 | A | | 11/1990 | Traitler et al. |
| 5,011,855 | A | | 4/1991 | Traitler et al. |
| 5,130,449 | A | * | 7/1992 | Lagarde et al. |
| 5,744,145 | A | * | 4/1998 | Bertoli et al. |
| 5,747,533 | A | * | 5/1998 | Egberg et al. |
| 6,248,352 | B1 | * | 6/2001 | Semeria et al. |
| 6,284,268 | B1 | * | 9/2001 | Mishra et al. |

FOREIGN PATENT DOCUMENTS

| | | |
|---|---|---|
| DE | 43 30 664 A1 | 3/1995 |
| EP | 0092085 A | 10/1983 |
| FR | 2 720 647 A1 | 12/1995 |
| FR | 2 773 484 A1 | 7/1999 |
| GB | 2 254 556 A | 10/1992 |

OTHER PUBLICATIONS

Sugiyama, M. et al., "Effect of Vitamin E on Cytotoxicity, DNA Single Strand Breaks, Chromosomal Aberrations, and Mutation in Chinese Hamster V–79 Cells Exposed to Ultraviolet–B Light", Photochemistry and Photobiology, vol. 56, No. 1, pp. 31–34, 1992.
Lopez–Torres, M. et al., "Topical application of a–tocopherol modulates the antioxidant network and diminishes ultraviolet–induce oxidative damage in muring skin", British Journal of Dermatology, 1998: 138: pp. 207–2215.
Kitazaqa, M. et al., "Interactions between Vitamin E Homoogues and Ascorbate Free Radicals in Murine Skin Homogenates Irradiated with Ultraviolet Light", Photochemistry and Photobiology 1997, 65(2): pp 355–365.
Meydani, M., "Vitamin E", The Lancet, vol. 345, Jan. 21, 1995, pp. 170–175.

Darr, D. et al., "Topical Vitamin C Protects Porcine Skin from Ultraviolet Radiation–Induced Damage", British Journal of Dermatology (1992) 127, 247–253.
Eberlein–Konig, B., MD, et al., Protective Effect Against Sunburn of Combined Systemic Ascorbic Acid (Vitamin C) and d–a–Tocopherol (Vitamin E), Journal of the American Academy of Dermatology, vol. 38, No. 1, 1998, pp. 45–48.
Someya, K., et al., "The Effect of Natural Carotenoid (Palm Fruit Carotene) Intake on Skin Lipid Peroxidation in Hairless Mice", J. Nutr. Sci. Viitaminol., 40, 303–314, 1994.
Alexander, M. et al., "Oral Beta–Carotene can Increase the Number of OKT4+ Cells in Human Blood", Immunology Letters, 9 (1985) 221–224.
Mathews–Roth, M. M., et al., "Systemic Photoprotection", Dermotologic Clinics, vol. 4, No. 2, Apr. 1986, pp 335–339.
Di Mascio, P., et al., "Lycopene as the Most Efficient Biological Carotenoid Singlet Oxygen quencher", Archives of Biochemistry and Biophysics, vol. 274, No. 2, Nov. 1, pp 532–538, 1989.
Neuman, R. et al., "Treatment of Polymorphous Light Eruption with Nicotinamide: a Pilot Study", British Journal of Dermatology (1986), 115, 77–80.
Guichardant, M. et al., "Stearidonic Acid, an Inhibitor of the 5–Lipoxygenase Pathway. A Comparison with TTimnodonic and Dihomogammalinolenic Acid", Lipids, vol. 28, No. 4 (1993) pp. 321–324.
Thiele, J. J. et al., "Ozone Depletes Tocopherols and Tocotrienols Topically Applied to Murine Skin", FEBS 401 (1997) 167–170.
Wu D., et al. "Effect of Dietary Supplementation with Black Currant Seed Oil on the Immune Response of Healthy Elderly Subjects" American Journal of Clinical Nutrition, Bethesda, MD, US, vol. 70, No. 4, Jul. 1999, pp. 536–543.
Ziboh, V. A., et al. "Dose–Response Effects of Dietary Gamma–Linolenic Acid–Enriched Oils on Human Polymorphonuclear–Neutrophil Biosynthesis of Leukotriene $B_41$–3" American Journal of Clinical Nutrition, Bethesda, MD, USA, vol. 55, No. 1, 1992, pp. 39–45.
Kitazawa, et al. "Interactions between Vitamin E Homologues and Ascorbate Free Radicals in Murine Skin Homogenates Irradiated with Ultraviolet Light" Photochemistry and Photobiology, 1997, vol. 65, No. 1, pp. 355–365.

(List continued on next page.)

Primary Examiner—Marianne C. Seidel
Assistant Examiner—Vickie Kim

(57) ABSTRACT

The present invention relates to the use of a composition comprising an oil with a high content of essential fatty acids of ω3 and ω6 type, preferably blackcurrant seed oil, and at least one compound selected from β-carotene, lycopene, tocopherol and its derivatives, tocotrienols and their derivatives, ascorbic acid and nicotinamide, as a nutritional supplement intended for preventing and/or combating the harmful effects of xenobiotics on the skin, in particular on the skin's immune system.

11 Claims, 2 Drawing Sheets

OTHER PUBLICATIONS

Figure 1:
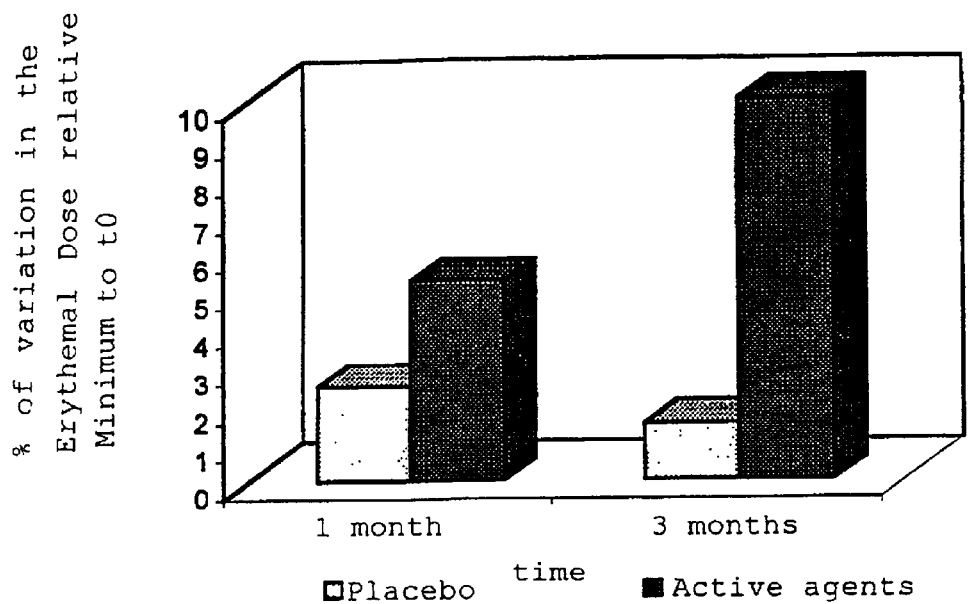

Paolo DiMascio, et al. "Lycopene as the Most Efficient Biological Cartenoid Singlet Oxygen Quencher" Biochemistry and Biophysics, vol. 274, No. 2, Nov. 1, pp. 532–538, 1989.

M. Lopez–Torres, et al. "Topical application of α–tocopherol modulates the antioxidant network and Dimishes Ultraviolet–induced Oxidative Damage in Murine Skin" British Journal of Dematology 1998, vol. 1, No. 38, pp. 207–215.

Michael Alexander, et al. "Oral Beta–Carotene Can Increase the Number of OKT4+ Cells in Human Blood" Elsevier Science Publishers B.V., Immunology Letters, vol. 9, 1985 pp. 221–224.

Micheline M. Mathews–Roth, M.D. "Systemic Photoprotection" Dermatologic Clinics, vol. 4 No. 2, Apr. 1986, pp. 335–339.

Masayasu Sugiyama et al. "Effect of Vitamin E on Cytotoxicity, DNA Single Strand Breaks, Chromosomal Aberrations, and mutation in Chinese hamster V–79 Cells Exposed to Ultraviolet–B Light" Photobiology vol. 56, No. 1, pp. 31–34, 1992.

R. Neumann, et al. "Treatment of polymorphous light eruption with nicotinamide: a pilot study" British Journal of Dermatology (1996), vol. 115, pp. 77–80.

Bernadette Eberlein–König, et al. "Protective Effect Against Sunburn of Combined systemic Ascorbic Acid (vitamin C) and d–α–tocopherol (vitamin E)" Jan. 1998, Jourmal of the American Academy of Dermatology, Inc., pp. 45–49.

Michael Guichardant, et al. "Stearidonic Acid, an Inhibitor of the 5 Lipoxygenase Pathway. A comparison with timnodonic and Dihomogammalinolenic Acid" American Oil Chemists' Society, LIPIDS, vol. 28, No. 4 (1993), pp. 321–324.

D. Darr, et al., Topical Vitamin C protects porcine skin for Ultraviolet Radiation–induced Damage, British Journal of Dermatology (1992), vol. 127, pp. 247–253.

Keita Someya, et al., The Effect of Natural Carotenoid (Palm Fruit Carotene) Intake on Skin Lipid Peroxidation in Hairless Mice" J. Nutr. Sci. Vitaminol, vol. 40, pp. 303–314, 1994.

Mohsen Meydani, "Vitamin E" The Lancet, vol. 345 Jan. 1, 1995, pp. 170–175.

* cited by examiner

NUTRITIONAL SUPPLEMENT BASED ON BLACKCURRENT SEED OIL

The present invention relates to the use of a composition comprising an oil with a high content of essential fatty acids of ω3 and ω6 type, preferably blackcurrant seed oil, and at least one compound selected from β-carotene, lycopene, tocopherol and its derivatives, tocotrienols and their derivatives, ascorbic acid and nicotinamide as a nutritional supplement intended for preventing and/or combating the harmful effects of xenobiotics on the skin, in particular on the skin's immune system.

The skin is continually in contact with xenobiotics, which are substances that are referred to as being foreign to the cell's natural metabolic pathways, such as medicinal products, pesticides, pollutants, tobacco or UV. The skin suffers daily attack when it is exposed to these agents, in particular to UV rays which cause immediate damage to the skin, such as sunburn, photosensitivity or immunosuppression reactions, but also long-term effects such as photoageing or skin tumours.

Most of these adverse effects are associated with the production of oxygenated free radicals. They have the property of depolymerizing certain skin constituents such as collagen or elastin, or else of degrading membrane lipids or DNA, which results in the production of endobiotics that are harmful to the skin, such as toxic metabolites or inflammation mediators which finally lead to a loss of integrity of the cell membranes. The action of xenobiotics and endobiotics is particularly important as regards the skin's immune defences. Specifically, a depletion of the Langerhans cells can result in a penetration of pathogens into the body without the general immune system being alerted. This results, for example, in a higher propensity for the appearance of infections via pathogens.

The use of compounds capable of inhibiting or neutralizing the action of xenobiotics and endobiotics, in particular oxygenated free radicals, might make it possible to reduce the skin damage induced.

Among these compounds, vitamins and essential fatty acids have, in a certain number of in vitro and in vivo studies, shown protective activity with respect to harmful xenobiotics and endobiotics.

α-Tocopherol has shown that it can prevent the oxidation of polyunsaturated fatty acids, which are essential components of cell membranes and are particularly sensitive to damage induced by free radicals (1). This compound also has anti-inflammatory activity by means of direct action on the enzymatic systems of the arachidonic cascade (2). Other components belonging to the tocotrienol family (α-, γ-tocotrienols and their derivatives) have shown noteworthy action in preventing cell damage associated with an exposure of the skin and the superficial body growths to free radicals and UV rays (3) and to ozone (4). In addition, it has been demonstrated that the role of tocopherols and tocotrienols is important as regards the activation of the immune system (5).

Ascorbic acid can also trap the oxygenated free radicals (more particularly singlet oxygen) involved in many oxidative processes which damage cells (6). In addition, α-tocopherol combined with ascorbic acid shows effects on increasing the Minimum Erythemal Dose (7).

β-Carotene is a vitamin A precursor which acts as a chemical screening agent (with an absorption maximum in the UVA and visible range) and protects against lipid peroxidation (8, 9). It is often used to prevent photodermatoses (10). In general, carotenoids (β-carotene, lycopene, lutein, zeaxanthin and astaxanthin) are also involved in modulating the immune system (WO 98/44808). Lycopene is also a free-radical trap (11) and nicotinamide is often used in the same way as a β-carotene against photodermatoses (12).

Blackcurrant seed oil, which contains essential fatty acids of (ω3 and ω6 type, has shown a certain level of efficacy in reducing certain inflammatory processes (13).

In the context of the present invention, it has been found, surprisingly, that a combination between blackcurrant seed oil and the abovementioned compounds has, in a nutritional composition, an advantageous effect for reducing the harmful action of both xenobiotics and endobiotics of the free-radical type or of the type generating free radicals, in particular by reinforcing the skin's immune defences. After repeated daily administration, such a composition affords protection to the Langerhans cells.

DESCRIPTION

Thus, the present invention relates to the use of a composition comprising an oil with a high content of essential fatty acids of the type ω3 and ω6 and at least one compound selected from β-carotene, lycopene, tocopherol and its derivatives, tocotrienols and their derivatives, ascorbic acid and its derivatives, nicotinamide and a trace element, as a nutritional supplement intended for reinforcing the immune defences of the skin and the superficial body growths.

More specifically, this nutritional supplement may be intended for preventing and/or combating the harmful effects of xenobiotics on the skin, in particular on the skin's immune system, in particular for reducing the cytotoxic effects of xenobiotics on the Langerhans cells. In this sense, the composition according to the invention is useful for combating or preventing photodermatoses, for improving the skin's tolerance to sunlight and for preventing ageing of the skin and the superficial body growths and their disequilibrium due to free radicals.

In one advantageous embodiment, the composition comprises blackcurrant seed oil, since this oil is rich in essential fatty acids of ω3 and ω6 type, in particular α-linoleic acid, α-linolenic acid and γ-linolenic acid.

This oil comprises:

| | | |
|---|---|---|
| Palmitic acid | C16:0 | 6–8% |
| Stearic acid | C18:0 | 1–2% |
| Oleic acid ω9 | C18:1,Δ9 | 9–13% |
| Linoleic acid ω6 | C18:2,Δ9,12 | 44–51% |
| γ-Linolenic acid ω6 | C18:3,Δ8,9,12 | 15–20% |
| α-Linolenic acid ω3 | C18:3,Δ9,12,15 | 12–14% |
| Stearidonic acid ω3 | C18:4,Δ6,9,12,15 | 2–4% |

Essentially, the ω3 fatty acids have a beneficial effect on erythema induced by UVB and are useful in the prevention of photocarcinogenesis. The ω6 fatty acids are particularly important in the context of the invention since they participate in keratinization.

Needless to say, an oil equivalent to blackcurrant seed oil in terms of the abovementioned essential fatty acid composition can be used in the dietary supplement described according to the invention.

In one preferred aspect of the invention, the composition comprises blackcurrant seed oil, β-carotene, lycopene, tocopherol or its derivatives, tocotrienols or their derivatives, ascorbic acid or its derivatives, and nicotinamide.

The composition can also comprise a trace element, preferably selenium in any form, in particular in the form of selenium-containing yeasts.

Selenium is a co-factor which increases the activity of glutathione peroxidase (GPX), protects cells against the harmful effects of organic and inorganic peroxides, and stabilizes membranes by becoming incorporated into the disulphide bridges, thus leading to a decrease in the amount of arachidonic acid released during the inflammatory response. Thus, this compound is also useful as a compound for protecting the skin against xenobiotics.

The composition advantageously comprises at least 25% by weight, preferably about 50%, of blackcurrant seed oil. It can also comprise:

at least 5% by weight, preferably 15 to 18%, of ascorbic acid;
at least 4% by weight, preferably about 8%, of lycopene;
at least 5% by weight, preferably about 10%, of selenium;
at least 2% by weight, preferably about 4%, of β-carotene;
at least 1% by weight, preferably about 3%, of nicotinamide;
and/or at least 1% by weight, preferably about 2%, of tocopherol or its derivatives, in particular tocopheryl acetate.

A composition according to the invention may thus comprise approximately, by weight:
53% blackcurrant seed oil,
4% β-carotene,
8% lycopene,
2.2% tocopheryl acetate,
15 to 18% ascorbic acid, and
3% nicotinamide;
and optionally about 10% by weight of selenium.

Among the excipients which are added, those preferably selected are yellow beeswax, soybean lecithin, glycerol, liquid paraffin and gelatin, preferably of marine nature.

Needless to say, it is possible to add to the composition any other active compound known in the prior art. Mention may be made, for example, of nucleic acids or nucleotides, amino acids, in particular lysine and arginine, peptides, sugars, in particular biologically active sugars, retinoids, plant extracts, in particular from green tea or from soybean, any extracts from plants rich in isoflavones, DHEA and melatonin.

The composition according to the invention can be in the form of gel capsules, soft capsules, sugar-coated or plain tablets, including delayed forms, suitable for oral administration. Thus, the invention relates to a composition as defined above.

KEY TO THE FIGURES

FIG. 1: Efficacy of the oral supplement according to the invention on an erythema induced by UV. Measurement of the variation in the 1-month and 3-month minimum erythemal dose.

Figure 2:
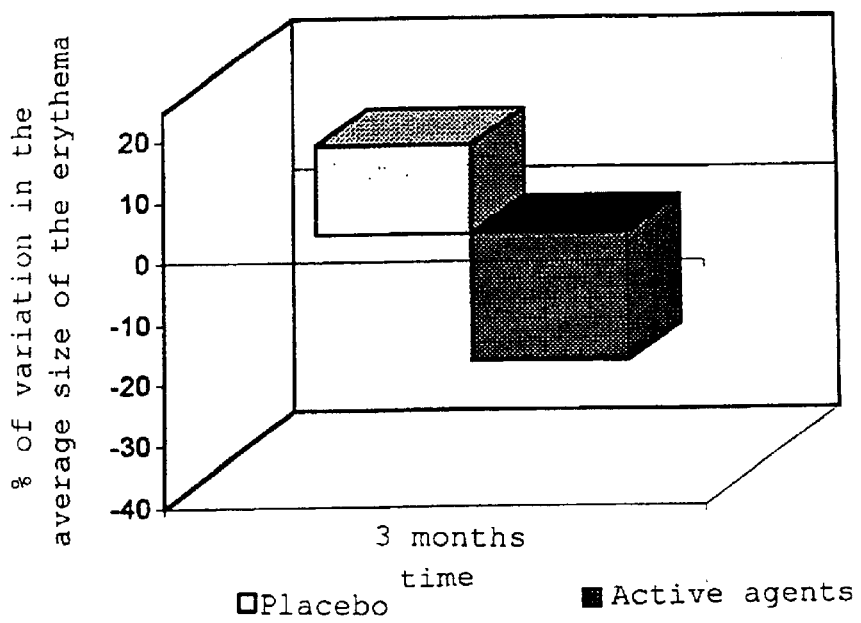

FIG. 2: Efficacy of the oral supplement according to the invention on an erythema induced by UV. Measurement of the variation in the average intensity of erythema at 3 months (oral composition+factor 16 antisun cream and placebo+factor 16 antisun cream).

Figure 3:
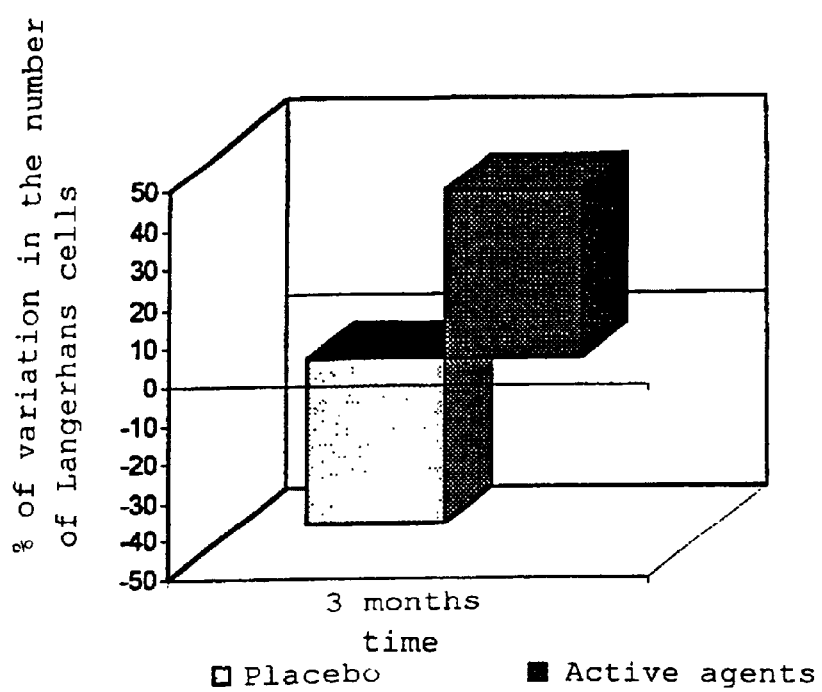

FIG. 3: Efficacy of the oral supplement according to the invention on the depletion of Langerhans cells induced by UV. Measurement of the variation in the number of Langerhans cells ($p<0.05$).

Figure 4:
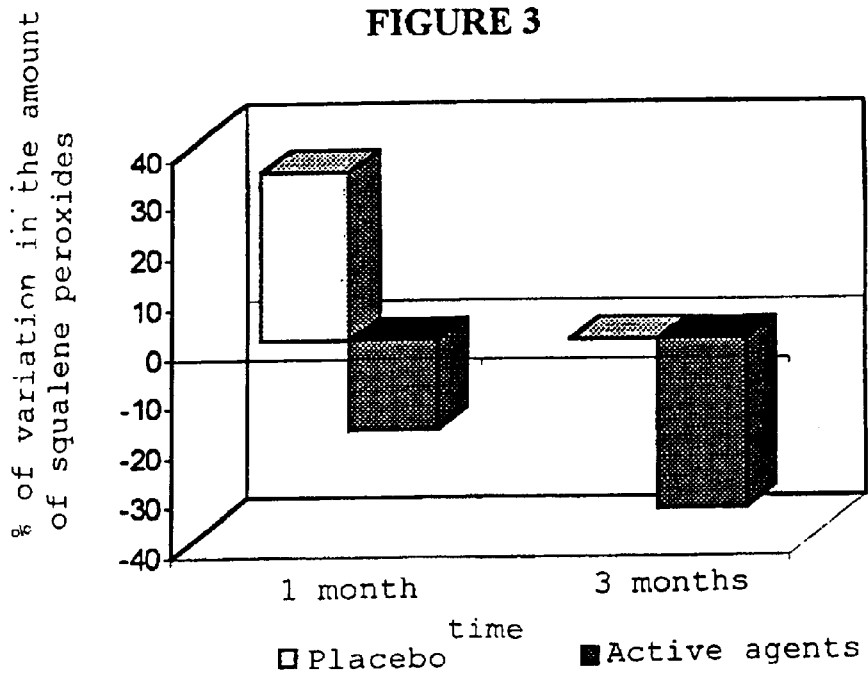

FIG. 4: Efficacy of the oral supplement according to the invention on lipid peroxidation. Measurement of the variation in the amount of squalene peroxides.

EXAMPLE 1

Preferred Composition No. 1 of the Invention

| | % by weight | Amount (mg/gel capsule) |
|---|---|---|
| Blackcurrant seed oil | 53% | 121.983 |
| 30% synthetic β-carotene | 4% | 9.2 |
| 6% lycopene | 8% | 19.167 |
| α-Tocopheryl acetate | 2.2% | 5.25 |
| Ascorbic acid | 15 to 18% | 34.5 to 42.0 |
| Nicotinamide | 3% | 6.9 |

Excipients:

| | |
|---|---|
| Yellow beeswax, soybean lecithin, glycerol, liquid paraffin, fish gelatin, dyes | qs 230 |

EXAMPLE 2

Preferred Composition No. 2 of the Invention

The composition is identical to the one described in Example 1, but in addition contains selenium≅10%; i.e. 23.5 mg/gel capsule.

EXAMPLE 3

Effects of the Composition on Protection Against Xenobiotics and on the Reinforcement of the Skin's Immune Defences, Demonstrated in a Double-blind Clinical Study Versus Placebo.

2 groups of 20 healthy volunteers including individuals with sensitive skin (minimum 8) were included after having signed a free, explained and express consent.
1st group (20 volunteers): 2 capsules containing the active agents taken orally per day for 90 consecutive days (3 months).
2nd group (20 volunteers): 2 capsules of the placebo (without active ingredients) taken orally per day for 90 days (3 months).
Measurements The Minimum Erythermal Dose (MED), or weakest perceptible redness with clearly defined edges, was determined on the back of the volunteers participating in the study, according to the recommendations of Colipa, before, 1 month after and 3 months after the start of the oral supplementation.

The capacity imparted by this supplementation to reinforce the protection afforded by an antisun cream (sun protection factor 16) was furthermore evaluated before and after the 3 months of treatment and was compared with the efficacy of the antisun cream alone.

Biopsies

Superficial skin samples were taken from the lower back of 10 volunteers from each group, using a circular bistoury (punch) 4 mm in diameter, 24 hours after irradiation with 1 MED.

The biopsies were then fixed with Bouin's fluid, included in paraffin and then sliced in series in order to be developed by immunohistochemistry to reveal the Langerhans cells (use of mouse clone 010 IgG1 monoclonal antibody, from the Immunotech laboratory, which recognises a specific membrane marker of the Langerhans cell, CD1a).

Results

All the results and the statistical comparisons are given in FIGS. 1–4 hereinbelow.

The oral supplementation studied significantly reinforces the skin's resistance to sunlight, compared with its placebo: increase in the minimum erythemal dose (FIG. 1), increase in the efficacy of a topical antisun screening agent (FIG. 2),
effect on the skin's immune system, by reducing the depletion of the Langerhans cells which is induced by UV (FIG. 3),
scavenging of the free radicals induced by UV (squalene hydroxyperoxides) (FIG. 4).

This combination of vitamins (α-tocopherol, ascorbic acid, β-carotene, lycopene and nicotinamide) and of blackcurrant seed oil which contains essential fatty acids thus appears to be indicated in the prevention of adverse effects induced by xenobiotics, in particular for reinforcing the skin's immune defences.

REFERENCES

1—SUGIYAMA M., DATSUYUKI K., MATSUMOTO R. et al, Effect of vitamin E on cytotoxicity, DNA single strand breaks, chromosomal aberration and mutation in Chinese hamster V-79 cells exposed to ultraviolet-B light. Photochem. Photobiol. 1992, 56 (1): 31–34.
2—LOPEZ-TORRES M., THIELE J. J., SHINDO Y. et al, Topical application of α-tocopherol modulates the antioxidant network and diminishes ultraviolet-induced oxidative damage in murine skin. Br. J. Dermatol. 1998, 138: 207–215.
3—KITAZAWA M. et al, Photochemistry and Photobiology, 1997, Vol 65: 355–365.
4—THIELE J. et al, FEBS LETTERS, Vol 401, January 20: 167–170.
5—MEYDANI M. The Lancet, Jan. 21, 1995, Vol 345, 170: 176
6—DARR D., COMBS S., et al, Topical vitamin C protects porcine skin from ultraviolet radiation-induced damage. Br. J. Dermatol. 1992, 127: 247–253.
7—EBERLEIN-KONIG, PLACZEC M., PRZYBILLA B. Protective effect against sunburn of combined systemic ascorbic acid (vitamin C) and d-α-tocopherol (vitamin B). J. Am. Acad. Dermatol. 1998, 38: 45–48.
8—SOMEYA K. The effect of natural carotenoid (palm fruit carotene) intake on skin lipid peroxidation in hairless mice. J. Nutr. Sci. Vitaminol. 1994, 410: 303–314.
9—ALEXANDER M., NEWMARK H. K, MILLER R. G. Oral β-carotene can increase the number of OKT4+ cells in human blood. Immunol. Lett. 1985, 9: 221–224.
10—MATHEWS-ROTH M. Systemic photoprotection. Dermatologic Clinics. 1986, 4 (2): 335–339.
11—DI MASCIO D. Lycopene as the most efficient biological cartenoid singlet oxygen quencher. Acta Biochem. Biophys. 1989, 274: 532–538.
12—NEUMANN R., RAPPOLD E., POHL-MARKL H. Treatment of polymorphous light eruption with nicotinamide: A pilot study. Br. J. Dermatol. 1986, 115: 77–80.
13—GUICHARDANT M., TRAITLER H., SPIELMAN D. et al. Stearidonic acid, an inhibitor of the 5-lipoxygenase pathway. A comparison with timnodonic and dihomogammalinoleic acid. Lipids. 1993, 28 (4): 321–324.

What is claimed is:

1. A method of reinforcing the immune defense of the skin by combating harmful effects of xenobiotics which result in photodermatoses and treating superficial body growths due to free radicals comprising administering orally to a mammal a composition consisting essentially of:

(a) an oil consisting essentially of at least about 15% ω6 essential fatty acid and at least about 12% ω3 essential fatty acid; and (b) at least one compound selected from the group consisting of β-carotene, lycopene, tocopherol, tocopherol derivatives, tocotrienol, tocotrienol derivatives, ascorbic acid, ascorbic acid derivatives, nicotinamide, one or more trace elements and mixtures thereof.

2. A method of reinforcing the immune defense of the skin by combating harmful effects of xenobiotics which result in photodermatoses and treating superficial body growths due to free radicals comprising administering orally to a mammal a composition consisting essentially of:

(a) at least about 25% by weight of blackcurrant seed oil;

(b) at least about 5% by weight of ascorbic acid;

(c) at least about 4% by weight of lycopene;

(d) at least about 1% by weight of tocopherol or its derivatives;

(e) at least about 1% by weight of nicotinamide; and (f) at least about 4% by weight of β-carotene.

3. A method of reinforcing the immune defense of the skin by combating harmful effects of xenobiotics which result in photodermatoses and treating superficial body growths due to free radicals comprising administering orally to a mammal a composition consisting essentially of:

(a) at least about 25% by weight of blackcurrant seed oil;

(b) from about 15% to about 18% by weight of ascorbic acid;

(c) at least about 4% by weight of lycopene;

(d) at least about 1% by weight of tocopherol or its derivatives;

(e) at least about 1% by weight of nicotinamide; and (f) at least about 4% by weight of β-carotene.

4. A method according to claim 3 wherein said composition contains at least 8% by weight of lycopene.

5. A method according to claim wherein said composition contains at least about 4% by weight of β-carotene.

6. A method according to claim wherein said composition contains at least about 3% by weight of nicotinamide.

7. A method according to claim 3 wherein said composition contains at least about 50% by weight of blackcurrant seed oil.

8. A method according to claim 3 wherein said composition is administered twice daily.

9. A method according to claim 3 wherein said composition consisting essentially of at least 50% blackcurrant seed oil, about 4% β-carotene, about 8% lycopene, about 2% tocopheryl acetate, about 15 to about 18% ascorbic acid and about 3% nicotinamide.

10. A method according to claim 3 wherein the said composition's effective dose is about 120mg/dose.

11. A method according to claim 10 wherein said dose is administered twice per day.

* * * * *